(12) United States Patent
Parris

(10) Patent No.: US 9,169,432 B2
(45) Date of Patent: Oct. 27, 2015

(54) SPREAD CROSSLINKER AND METHOD OF WATER CONTROL DOWNHOLE

(75) Inventor: Michael D. Parris, Richmond, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 468 days.

(21) Appl. No.: 13/537,402

(22) Filed: Jun. 29, 2012

(65) Prior Publication Data

US 2014/0005081 A1 Jan. 2, 2014

(51) Int. Cl.
| | |
|---|---|
| *C09K 8/68* | (2006.01) |
| *C09K 8/22* | (2006.01) |
| *C09K 8/88* | (2006.01) |
| *C09K 8/90* | (2006.01) |

(52) U.S. Cl.
CPC . *C09K 8/685* (2013.01); *C09K 8/68* (2013.01); *C09K 8/887* (2013.01); *C09K 8/90* (2013.01)

(58) Field of Classification Search
CPC ...... C09K 8/512; C09K 8/685; C09K 8/5756; C09K 8/887
USPC .......................................... 507/139, 217, 266
See application file for complete search history.

(56) References Cited

U.S. PATENT DOCUMENTS

| | | | |
|---|---|---|---|
| 3,692,676 A | 9/1972 | Culter et al. | |
| 4,539,048 A | 9/1985 | Cohen et al. | |
| 4,539,049 A | 9/1985 | Cohen | |
| 4,764,632 A | 8/1988 | Cohen | |
| 4,917,186 A | 4/1990 | Mumallah | |
| 5,304,620 A | 4/1994 | Holtmyer et al. | |
| 5,468,791 A | 11/1995 | Yuan | |
| 5,551,516 A | 9/1996 | Norman et al. | |
| 6,011,075 A | 1/2000 | Parris et al. | |
| 6,239,183 B1 | 5/2001 | Farmer et al. | |
| 6,482,866 B1 | 11/2002 | Dahayanake et al. | |
| 6,498,988 B1 | 12/2002 | Robert et al. | |
| 6,506,710 B1 | 1/2003 | Hoey et al. | |
| 6,703,352 B2 | 3/2004 | Dahayanake et al. | |
| 7,303,018 B2 | 12/2007 | Cawiezel et al. | |
| 2005/0031545 A1* | 2/2005 | Ebright et al. | 424/9.365 |
| 2006/0162928 A1 | 7/2006 | Collins et al. | |
| 2008/0058498 A1* | 3/2008 | Tsuboyama et al. | 528/395 |
| 2010/0099913 A1 | 4/2010 | Sun et al. | |

FOREIGN PATENT DOCUMENTS

| | | |
|---|---|---|
| EP | 135566 B1 | 3/1990 |
| GB | 1588521 A | 4/1981 |
| GB | 2322865 B | 9/1998 |

(Continued)

OTHER PUBLICATIONS

International Search Report and Written Opinion mailed on Aug. 28, 2013 for International Patent Application No. PCT/US2013/045099, filed on Jun. 11, 2013, 11 pages.

(Continued)

*Primary Examiner* — Aiqun Li
(74) *Attorney, Agent, or Firm* — Jeremy D. Tillman; Rachel E. Greene; Tim Curington

(57) ABSTRACT

A crosslinker composition including a spread crosslinker for treating a subterranean formation is provided along with methods of sealing a subterranean formation including introducing a crosslinkable fluid, the crosslinkable fluid containing a spread crosslinker and a crosslinkable component, into a subterranean formation.

26 Claims, 3 Drawing Sheets

(56) References Cited

FOREIGN PATENT DOCUMENTS

WO 8801991 A1 3/1988
WO WO2006095291 9/2006

OTHER PUBLICATIONS

Kirk et al. Enclyclopedia of Chemical Technology, Third Edition; vol. 16 248-273 (1981).

Harry et al., Chemical Structures of Group 4 Metal Crosslinkers for Polygalactomannans, paper SPE50731, 1999 SPE International Symposium on Oilfield Chemistry, Houston, TX.

Tackett, J.E., Characterizaton of Chromium (III) Acetate in Aqueous Solution, Applied Spectroscopy, vol. 43, Issue 3, pp. 490-499 (1989).

Kramer, J., et al, Comparisons of galactomannan crosslinking with organotitanates and borates, Colloid and Polymer Sci., vol. 266, No. 2, pp. 144-155,(1988).

* cited by examiner

SPREAD CROSSLINKER AND METHOD OF WATER CONTROL DOWNHOLE

BACKGROUND

Hydrocarbons (oil, natural gas, etc.) are obtained from a subterranean geologic formation (a "reservoir") by drilling a well that penetrates the hydrocarbon-bearing formation. In the process of recovering hydrocarbons from subterranean formations, it is common practice to treat a hydrocarbon-bearing formation with a pressurized fluid to provide flow channels, i.e., to fracture the formation, or to use such fluids to transport and place proppant to facilitate flow of the hydrocarbons to the wellbore.

Well treatment fluids, particularly those used in fracturing, may comprise a water or oil based fluid incorporating a thickening agent, normally a polymeric material. Typical polymeric thickening agents for use in such fluids comprise galactomannan gums, such as guar and substituted guars such as hydroxypropyl guar and carboxymethylhydroxypropyl guar (CMHPG). Cellulosic polymers such as carboxymethyl cellulose may also be used, as well as synthetic polymers such as polyacrylamide. To increase the viscosity, and, therefore, the proppant carrying ability of the fracturing fluid, as well as increase its high temperature stability, the polymeric materials may be crosslinked. Crosslinking a polymer solution may increase the steady shear viscosity up to two orders of magnitude. For well stimulation treatments, particularly hydraulic fracturing, this may creating fracture width and transporting and place proppant in the fracture.

By necessity, well treatment fluids are prepared on the surface, and then pumped through tubing in the wellbore to the hydrocarbon-bearing subterranean formation. While high viscosity, thickened fluid is highly desirable within the formation in order to transfer hydraulic pressure efficiently to the rock and to reduce fluid leak-off, large amounts of energy are consumed to pump such fluids through the tubing into the formation. To reduce the amount of energy consumed, various methods of delaying crosslinking have been developed. For example, metal complexing ligands, sometimes termed a chelant, may be employed to initially bind the metal, but on a controlled basis, and subsequently exchanged for coordination of the polymer by the metal. When two separate polymer molecules, or strands, are complexed by the metal, viscosity builds through the three-dimensional network. Other crosslinking delay methods which have been employed include physical sequestration of the crosslinker from the polymer by means such as encapsulating, or coating, the crosslinker, or delaying its contact into the polymer-bearing phase by emulsifying it. Other methods include dissolution controlled release of slowly soluble, crosslinker-containing solids, and delayed alteration of the pH of the combined polymer/crosslinker solution. These techniques allow the pumping of a relatively less viscous fluid having relatively low friction pressures within the well tubing with crosslinking being effected near or in the formation so that the properties of thickened crosslinked fluid are available at the rock face.

During the process of obtaining hydrocarbons (including the acts described above), undesirable materials, such as water, may also travel through the formation in the vicinity of the wellbore and ultimately enter the wellbore. The presence of water may be an issue in numerous formations, such as, for example, sand, sandstone, chalk, limestone, etc. The rate at which the water appears in the wellbore may be slowed through the use of various technologies directed to preventing undesirable materials from entering the wellbore. Conventional water shut off techniques range from mechanical to chemical treatment strategies.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In some embodiments, the present disclosure relates to a fluid for treating a subterranean formation including a solvent, a crosslinkable component, and a crosslinking composition comprising a spread crosslinker, the spread crosslinker having a headgroups separated by an intervening spacer that is covalently bound to the headgroups, where headgroups may include a first head group having at least one ring of at least five atoms, where at least two of the atoms in the at least one ring of the first headgroup are chelated polyvalent metal atoms, and a second headgroup having at least one ring of at least five atoms, where at least two of the atoms in the at least one ring of the second headgroup are chelated polyvalent metal atoms. The present disclosure also relates to a method of treating a subterranean zone penetrated by a well bore that includes contacting the subterranean zone with this fluid for treating a subterranean formation.

In some embodiments, the present disclosure relates to a crosslinking composition including a spread crosslinker and methods of treating a wellbore including permeating at least a portion of a subterranean formation with the crosslinking composition.

BRIEF DESCRIPTION OF THE DRAWINGS

The manner in which the objectives of the present disclosure and other desirable characteristics may be obtained is explained in the following description and attached drawings in which.

DETAILED DESCRIPTION

Figure 1:
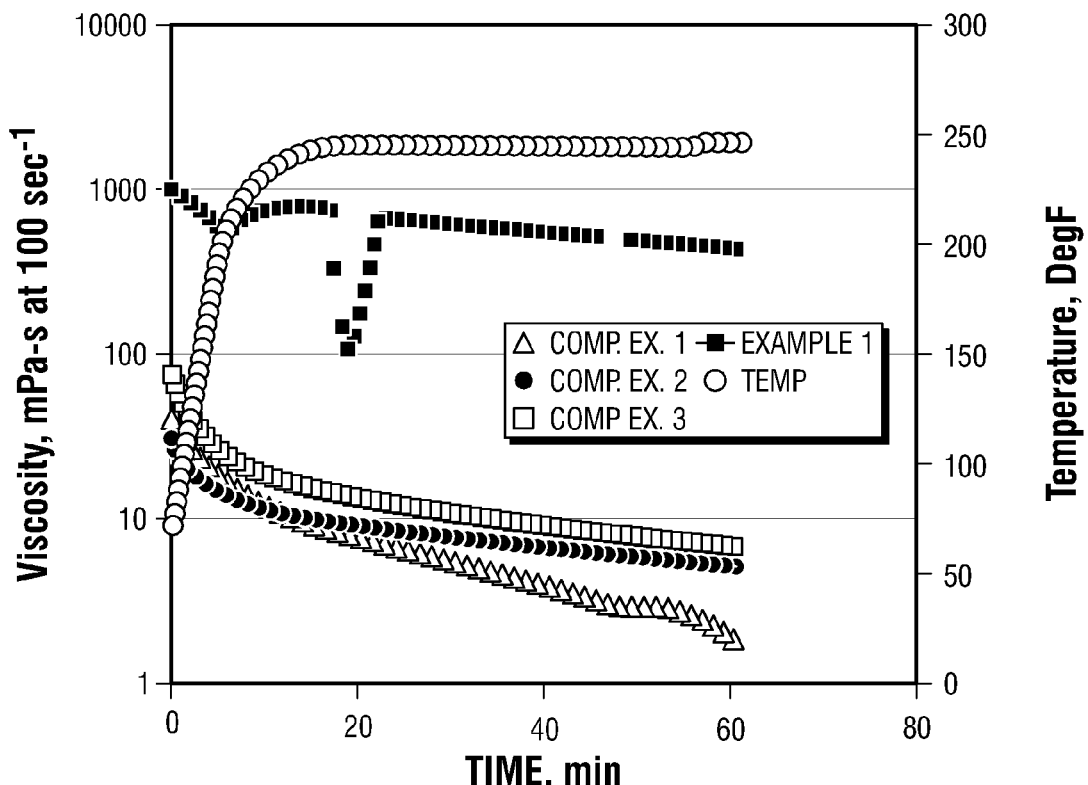
FIG. 1 is an illustration of the rheology profiles of the solutions prepared in Example 1 and Comparative Examples 1-3.

In the following description, numerous details are set forth to provide an understanding of the present disclosure. However, it may be understood by those skilled in the art that the methods of the present disclosure may be practiced without these details and that numerous variations or modifications from the described embodiments may be possible.

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a range listed or described as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Furthermore, one or more of the data points in the present examples may be combined together, or may be combined with one of the data points in the specification to create a range, and thus include each possible value or number within this range. Thus, even if a specific data points within the range, or even no data points within the range, are explicitly identified or refer to a few specific, it is to be understood that inventors appreciate and understand that any conceivable data point within the range is to be considered to have been specified, and that inventors possessed knowledge of the entire range and each conceivable point and sub-range within the range.

The present disclosure relates generally to a spread crosslinker for use in downhole applications, such as crosslinking materials in subterranean formations, treating hydrocarbon-bearing rock formations, sealing hydrocarbon-bearing rock formations and/or controlling fluids in hydrocarbon-bearing rock formations to minimize flow of an unacceptable amount of material/fluid (such as water), into a predetermined area, such as into a wellbore.

The present disclosure also relates to methods of controlling water in a subterranean formation, such as subterranean formations found in oil fields. The methods of the present disclosure may comprise introducing a crosslinkable fluid including a crosslinking composition comprising a spread crosslinker, such as a dual-headed or homobifunctional crosslinking agent comprising one or more chelated polyvalent metals, and one or more crosslinkable components or materials into a subterranean formation. For example, the crosslinkable fluid may be introduced, injected or conveyed into a subterranean formation by way of a wellbore that penetrates a subterranean formation, such as a water-bearing subterranean formation.

The subject matter of the present application also relates to well servicing methods that may be applied at any time in the life cycle of a reservoir or field to enhance the value of oil and gas assets through reduced water handling cost, improved hydrocarbon productivity and/or higher recovery factors. As used herein, the term "field" includes land based (surface and sub-surface) and sub-seabed applications. The term "oilfield," as used herein, includes hydrocarbon oil and gas reservoirs, and formations or portions of formations where hydrocarbon oil and gas are expected but may ultimately contain water, brine, or some other composition.

As used herein, the phrases "crosslinkable fluid," "treatment fluid" or "fluid for treatment" (hereinafter generally referred to as a "crosslinkable fluid" unless specified otherwise) mean, for example, a composition comprising a solvent, a crosslinkable material, which includes any crosslinkable compound and/or substance with a crosslinkable moiety, (hereinafter "crosslinkable component") that may be substantially inert to any produced fluids (gases and liquids) and other fluids injected into the wellbore or around the wellbore, such as workover fluids, and a crosslinking composition which comprises a crosslinker, for example, to seal at least a portion of the area into which the crosslinkable fluid is pumped.

The crosslinkable fluid of the present disclosure may be a solution initially having a very low viscosity that can be readily pumped or otherwise handled. For example, the viscosity of the crosslinkable fluid may be from about 1 cP to about 10,000 cP, or be from about 1 cP to about 1,000 cP, or be from about 1 cP to about 100 cP at the treating temperature, which may range from a surface temperature to a bottom-hole static (reservoir) temperature, such as from about 4° C. to about 80° C., or from about 10° C. to about 70° C., or from about 25° C. to about 60° C., or from about 32° C. to about 55° C.

Crosslinking the crosslinkable fluid of the present disclosure generally increases its viscosity. As such, having the composition in the uncrosslinked/unviscosified state allows for pumping of a relatively less viscous fluid having relatively low friction pressures within the well tubing, and the crosslinking may be delayed in a controllable manner such that the properties of thickened crosslinked fluid are available at the rock face instead of within the wellbore. Such a transition to a crosslinked/uncrosslinked state may be achieved over a period of minutes or hours based on the particular molecular make-up of the spread crosslinker, and results in the initial viscosity of the crosslinkable fluid increasing by at least an order of magnitude, such as at least two orders of magnitude.

Suitable solvents for use with the crosslinkable fluid in the present disclosure may be aqueous or organic based. Aqueous solvents may include at least one of fresh water, sea water, brine, mixtures of water and water-soluble organic compounds and mixtures thereof. Organic solvents may include any organic solvent with is able to dissolve or suspend the various components of the crosslinkable fluid.

In some embodiments, the crosslinkable fluid may initially have a viscosity similar to that of the aqueous solvent, such as water. An initial water-like viscosity may allow the solution to effectively penetrate voids, small pores, and crevices, such as encountered in fine sands, coarse silts, and other formations. In other embodiments, the viscosity may be varied to obtain a desired degree of flow sufficient for decreasing the flow of water through or increasing the load-bearing capacity of a formation. The rate at which the viscosity of the crosslinkable fluid changes may be varied by the choice of the spread crosslinker and polymer employed in the crosslinkable fluid. The viscosity of the crosslinkable fluid may also be varied by increasing or decreasing the amount of solvent relative to other components, or by other techniques, such as by employing viscosifying agents. In embodiments, the solvent, such as an aqueous solvent, may represent up to about 99.9 weight percent of the crosslinkable fluid, such as in the range of from about 85 to about 99.9 weight percent of the crosslinkable fluid, or from about 98 to about 99.7 weight percent of the crosslinkable fluid.

The crosslinkable fluids or compositions suitable for use in the methods of the present disclosure comprise a crosslinkable component. As discussed above, a "crosslinkable component," as the term is used herein, is a compound and/or substance that comprises a crosslinkable moiety. For example, the crosslinkable components may contain one or more crosslinkable moieties, such as a carboxylate and/or a cis-hydroxyl (vicinal hydroxyl) moiety, that is able to coordinate with the reactive sites of the spread crosslinker. The reactive sites of the spread crosslinker may be, for example, the site where the metals (such as Al, Zr and Ti and/or other Group IV metals) are present. The crosslinkable component may be natural or synthetic polymers (or derivatives thereof) that comprise a crosslinkable moiety, for example, substituted galactomannans, guar gums, high-molecular weight polysaccharides composed of mannose and galactose sugars, or guar derivatives, such as hydrophobically modified guars, guar-containing compounds, and synthetic polymers. Suitable crosslinkable components may comprise a guar gum, a locust bean gum, a tara gum, a honey locust gum, a tamarind gum, a karaya gum, an arabic gum, a ghatti gum, a tragacanth gum, a carrageenen, a succinoglycan, a xanthan, a diutan, a hydroxylethylguar hydroxypropyl guar, a carboxymethylhydroxyethyl guar, a carboxymethylhydroxypropylguar, an alkylcarboxyalkyl cellulose, an alkyl cellulose, an alkylhydroxyalkyl cellulose, a carboxyalkyl cellulose ether, a hydroxyethylcellulose, a carboxymethylhydroxyethyl cellulose, a carboxymethyl starch, a copolymer of 2-acrylamido-2-methyl-propane sulfonic acid and acrylamide, a terpolymer of 2-acrylamido-2-methyl-propane sulfonic acid, acrylic acid, acrylamide, or derivative thereof. In embodiments, the crosslinkable components may present at about 0.01% to about 4.0% by weight based on the total weight of the crosslinkable fluid, such as at about 0.10% to about 2.0% by weight based on the total weight of the crosslinkable fluid.

The term "derivative" herein refers, for example, to compounds that are derived from another compound and maintain the same general structure as the compound from which they are derived.

Upon selection of the appropriate crosslinkable component (for example, in view of factors such as the downhole environment and desired application) to be incorporated into the crosslinkable fluid of the present disclosure, crosslinking may be accomplished through the assistance of a crosslinking composition comprising a "spread crosslinker."

The term "spread crosslinker" means, for example, a single molecule with multiple active crosslinking groups, spread spatially by intervening atoms. In embodiments, the spread crosslinker is a single molecule in which two or more polyvalent metals, such as aluminum, zirconium, titanium, or Group IV metals, are separated on a single molecule with an intervening spacer. The polyvalent metal, such as aluminum, zirconium, titanium, or Group IV metals, may serve as a reactive site that is capable of reacting with a crosslinkable moiety on a crosslinkable component.

The spread crosslinkers of the present disclosure are not limited with respect to the number of polyvalent metal atoms (such as aluminum, zirconium, titanium, or Group IV metals) that are present on a single molecule and may serve as a reactive site. Furthermore, the spread crosslinkers of the present disclosure may include either a single type (homofunctional) or multiple types (heterofunctional) of reactive sites (such as metal atoms such as Al, Zr and Ti and/or other Group IV metals) capable of reacting with a crosslinkable moiety on a crosslinkable component. Multiple types of reactive sites may occur, for example, when more than one type of metal atom (such as Al, Zr and Ti and/or other Group IV metals) is present in a single spread crosslinker.

Homofunctional spread crosslinkers include spread crosslinkers in which each of the polyvalent metal atoms in the molecule is the same such that the reactive sites and/or coordinating groups may be the same. For instance, such a homofunctional spread crosslinker may be homobifunctional, homotrifunctional, homotetrafunctional, or poly-homofunctional. A homobifunctional, homotrifunctional, or homotetrafunctional spread crosslinker is a molecule with two, three, or four similar reactive sites and/or coordinating groups, respectively. Likewise, a poly-homofunctional spread crosslinker is a molecule with two or more similar reactive sites and/or coordinating groups, such as a polymeric spread crosslinker including two or more similar reactive sites (metal atoms such as Al, Zr and Ti and/or other Group IV metals) and/or coordinating groups distributed on the repeat units thereof.

The spread crosslinker may also be heterofunctional (such as heterobifunctional, heterotrifunctional or poly-heterofunctional, which is a molecule with two or more dissimilar reactive sites (metal atoms such as Al, Zr and Ti and/or other Group IV metals) and/or coordinating groups. A heterobifunctional or heterotrifunctional spread crosslinker is a molecule with two or three dissimilar reactive sites (metal atoms such as Al, Zr and Ti and/or other Group IV metals) and/or coordinating groups, respectively. Likewise, a poly-heterofunctional spread crosslinker is a molecule with two or more dissimilar reactive sites and/or coordinating groups, such as a polymeric spread crosslinker including two or more dissimilar reactive sites (metal atoms such as Al, Zr and Ti and/or other Group IV metals) and/or coordinating groups distributed on the repeat units thereof.

These similar or dissimilar reactive sites may be separated on the spread crosslinker by a non-reacting intervening spacer, such as an alkylene group, arylene group, arylalkylene group, alkylarylene group, or repeating units of the polymer, which is designed to provide the desired distance between the reactive sites, which may be metals, such as Al, Zr and Ti and/or other Group IV metals.

A polymeric spread crosslinker may contain about 5 to about 1000 repeating units, or from about 10 to about 100 repeating units, in which two or more of the repeating units include a reactive site (metal atoms such as Al, Zr and Ti and/or other Group IV metals) and/or coordinating group. Such polymeric spread crosslinker may be obtained from polymerizing monomer units functionalized with metal atoms such as Al, Zr and Ti and/or other Group IV metals before polymerization, or may be derived from functionalizing the repeat units of the polymer after polymerization, such that the metal atoms are regularly or randomly distributed in the polymer molecule.

Additionally, spread crosslinkers of the present disclosure may include spreading reactive sites (metal atoms such as Al, Zr and Ti and/or other Group IV metals) and/or coordinating groups distributed on a colloidal or nanometric substrate, such as silica or latex. Such spread crosslinkers may be obtained by functionalizing the surface of the colloid with reactive sites capable of reacting with a crosslinkable moiety on a crosslinkable component.

Spread crosslinkers that may be used in accordance with the present disclosure may also include single molecules having at least two headgroups bound (either covalently and/or ionically) to one or more intervening spacers. Such a structure may be represented by: (headgroup)$_m$-(intervening spacer), where m may be any suitable integer depending on the size of the intervening spacer, such as an integer from about 2 to about 20, an integer from about 2 to about 8, or an integer from about 2 to about 6, and the headgroups may be the same or different.

In some embodiments, the spread crosslinkers may contain a first and a second headgroup, each with reactive sites (the reactive sites being capable of reacting with a crosslinkable moiety on a crosslinkable component), separated by an intervening spacer that is bound (either covalently and/or ionically) to the first and second headgroups.

The term "headgroup" means, for example, a structure including one or more polyvalent metal atoms, such as heterocyclic ring structure, which may or may not be a polycyclic ring structure, including one or more polyvalent metals. The following structure is an illustration of a molecule having a first and a second head group:

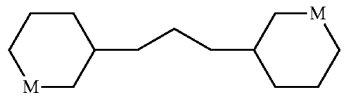

In the above structure, two six membered rings (M is a polyvalent metal), which are the first headgroup and second headgroup, are separated by an intervening alkyl spacer. As discussed above, the spread crosslinkers of the present disclosure are not limited to bifunctionality, but may be polyfunctional, with either a single type or multiple types of reactive sites.

In embodiments, the first headgroup and/or second headgroup of the spread crosslinker may comprise at least one ring of at least five atoms, such as at least one ring of at least six atoms. In embodiments, at least two of the atoms in the at least one ring of the first headgroup and/or second headgroup are chelated polyvalent metal atoms. In embodiments, at least one of the atoms in the at least one ring of the first headgroup and/or second headgroup is an oxygen atom. In some embodiments, at least two of the atoms in the at least one ring of the first headgroup and/or second headgroup are oxygen atoms. In further embodiments, at least three of the atoms in the at least one ring of the first headgroup and/or second headgroup are oxygen atoms.

For example, in such a specific embodiment where the first headgroup and/or the second headgroup of the spread crosslinker includes one ring of six atoms, the identity of the six atoms may be as follows: two of the six atoms may be chelated polyvalent metal atoms, three of the atoms may be oxygen, and the remaining atom may be a carbon atom.

In embodiments, the spread crosslinker may be a single molecule (where the first and the second headgroup are separated with an intervening spacer) in which four or more polyvalent metals are spread on a single molecule. For example, two polyvalent metals (capable of crosslinking with the crosslinkable component) may be present on the first head group of the spread crosslinker and two polyvalent metals (capable of crosslinking with the crosslinkable component) may be present on the second head group of the spread crosslinker. The polyvalent metals that are spread on a single spread crosslinker may be the same or different.

In embodiments, the first and/or second headgroup of the spread crosslinker comprises at least one ring of at least five atoms where at least one of the atoms in the at least one ring of the first headgroup is a chelated metal atom. For example, the first and/or second headgroup of the spread crosslinker may contain two or more rings with each ring containing five, six, or seven atoms where at least one of the atoms in the two or more rings of the first and/or second headgroup is a chelated metal atom, or at least two of the atoms in the two or more rings of the first and/or second headgroup are chelated polyvalent metal atoms. For example, the first and/or second headgroup of such a spread crosslinker may be similar to a naphthalene or anthracene structure where at least two of the atoms in the a naphthalene or anthracene structure are chelated polyvalent metal atoms (further hetero atoms either may or may not be present).

In some embodiments, the first and/or second headgroup comprises at least one ring of at least five atoms where at least two of the atoms in the at least one ring of the first headgroup are chelated polyvalent metal atoms. For example, the first and/or second headgroup may contain two or more rings with each ring containing five, six, or seven atoms where at least two of the atoms in the two or more rings of the first and/or second headgroup are chelated polyvalent metal atoms.

The polyvalent metals may be selected based on their ability to crosslink the crosslinkable component. For example, in embodiments, polyvalent metals may be selected for the crosslinking reaction between the crosslinkable components, such that the crosslinking reaction may be either reversible or irreversible. The polyvalent metals may be selected from the group consisting of aluminum, titanium and zirconium. In embodiments, the crosslinking reaction between the spread crosslinker (such as a spread crosslinker comprising aluminum) and the crosslinkable component forms a crosslinked material that may be de-crosslinked by supplying thermal energy.

In embodiments, intervening spacer may be (a) an alkylene group, such as an alkylene group having 1 to about 40 carbon atoms, such as about 4 to about 20 carbon atoms, or about 6 to about 10 carbon atoms, wherein hetero atoms either may or may not be present in the alkylene group; (b) an arylene group, such as an arylene group having about 5 to about 40 carbon atoms, such as about 6 to about 14 carbon atoms, or about 6 to about 10 carbon atoms, wherein hetero atoms either may or may not be present in the arylene group; (c) an arylalkylene group, such as an arylalkylene group having about 6 to about 40 carbon atoms, such as about 7 to about 22 carbon atoms, or about 7 to about 20 carbon atoms, wherein hetero atoms either may or may not be present in either or both of the alkyl portion and the aryl portion of the arylalkylene group; or (d) an alkylarylene group, such as an arylalkylene group having about 6 to about 40 carbon atoms, such as about 7 to about 22 carbon atoms, or about 7 to about 20 carbon atoms, wherein hetero atoms either may or may not be present in either or both of the alkyl portion and the aryl portion of the alkylarylene group.

The term "alkylene" refers, for example, to a divalent aliphatic group or alkyl group, including linear and branched, saturated and unsaturated, cyclic and acyclic, and substituted and unsubstituted alkylene groups, and wherein heteroatoms, such as oxygen, nitrogen, sulfur, silicon, phosphorus, boron, Mg, Li, Ge, Cu, Fe, Ni, Pd, Pt and the like either may or may not be present in the alkylene group. For example, an alkylene group may have the structure $(CH_2)_n$, in which n is an integer in a range of from 1 to about 40, such as from about 4 to about 25, or about 6 to about 15.

The term "arylene" refers, for example, to a divalent aromatic group or aryl group, including substituted and unsubstituted arylene groups, and wherein heteroatoms, such as O, N, S, P, Si, B, Li, Mg, Cu, Fe and the like either may or may not be present in the arylene group. For example, an arylene group may have about 5 to about 40 carbon atoms in the arylene chain, such as from about 6 to about 14 or from about 6 to about 10 carbon atoms.

The term "arylalkylene" refers, for example, to a divalent arylalkyl group, including substituted and unsubstituted arylalkylene groups, wherein the alkyl portion of the arylalkylene group can be linear or branched, saturated or unsaturated, and cyclic or acyclic, and wherein heteroatoms, such as O, N, S, P, Si, B, Li, Mg, Cu, Fe, and the like either may or may not be present in either the aryl or the alkyl portion of the arylalkylene group. For example, an arylalkylene group may have about 6 to about 40 carbon atoms in the arylalkylene chain, such as from about 7 to about 22 or from about 7 to about 20 carbon atoms.

The term "alkylarylene" refers, for example, to a divalent alkylaryl group, including substituted and unsubstituted alkylarylene groups, wherein the alkyl portion of the alkylarylene group can be linear or branched, saturated or unsaturated, and cyclic or acyclic, and wherein heteroatoms, such as O, N, S, P, Si, Ge, B, Li, Mg, Cu, Fe, Pd, Pt and the like either may or may not be present in either the aryl or the alkyl portion of the alkylarylene group. For example, the alkylarylene may have about 6 to about 40 carbon atoms in the alkylarylene chain, such as from about 7 to about 22 or from about 7 to about 20 carbon atoms.

The substituents on the substituted alkylene, arylene, arylalkylene, and alkylarylene groups can be, for example, halogen atoms, ether groups, aldehyde groups, ketone groups, ester groups, amide groups, imide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, cyano groups, pyridine groups, pyridinium groups, guanidinium groups, amidine groups, imidazolium groups, carboxylate groups, carboxylic acid groups, urethane groups, urea groups, and mixtures thereof.

The first and/or second headgroup of the spread crosslinker of the present disclosure may include one or more chelated polyvalent metal atoms. In embodiments, the chelated polyvalent metal atoms of the first and/or second headgroup include one or more ligands that coordinate with the polyvalent metal atoms. The ligands may be organic groups that may form a unidentate complex, or a polydentate complex, such as, for example, a bidentate complex, and a tridentate complex, with the polyvalent metal atoms of the spread crosslinker. For example, a bidentate chelating agent can be ethylmalonic acid, N,N-dimethylethylenediamine, trimethylenediamine or ethylenediamine. Examples of tridentate chelating agents include diethanolamine, diethylenetriamine or aminodiacetic acid. Examples of polydentate chelating agents include triethanolamine, ammoniatriacetic acid, ethylenediamine tetraacetic acid or ethylenediaminetetrapropionic acid.

Further chelating agents that may be suitable to form the chelated polyvalent metal atoms of the first and/or second headgroups of the spread crosslinker of the present disclosure may include carboxylic acids, aminocarboxylic acids, polyols, alkanolamines, glutamic acid, lactic acid, triethanolamine, alanine, aspartic acid, oxalic acid, acetylacetonate, fumaric acid, bis-hydroxyethylglycine, maleic acid, tartaric acid, citric acid, nitrilotriacetic acid, hydroxyethyliminodiacetic acid, hydroxyethylethylenediaminetetraacetic acid, ethylenediaminetetraacetic acid, cyclohexylenediaminetetraacetic acid, diethylenetriaminepentaacetic, hydroxyethylethylenediaminetriacetic acid, diethylenetriaminepentaacetic acid, propylenediaminetetraacetic acid, ethylenediaminedi(o-hydroxyphenylacetic) acid, ammonium salts thereof, lithium salts thereof, sodium salts thereof, and mixtures thereof.

In embodiments, the spread crosslinker comprises one or more compounds obtained by reacting one or more chelating agents with a compound containing various complementary functional groups that react with the functional groups of the chelating agent to obtain a single molecule in which two or more polyvalent metals, such as aluminum, zirconium, titanium, or Group IV metals, are spread on a single molecule with an intervening spacer. For example, such a spread crosslinker may be obtained by reacting a chelating agent, such as citric acid, with a compound of the formula I:

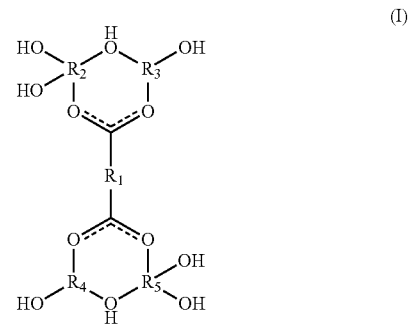

(I)

to yield a spread crosslinker formula II:

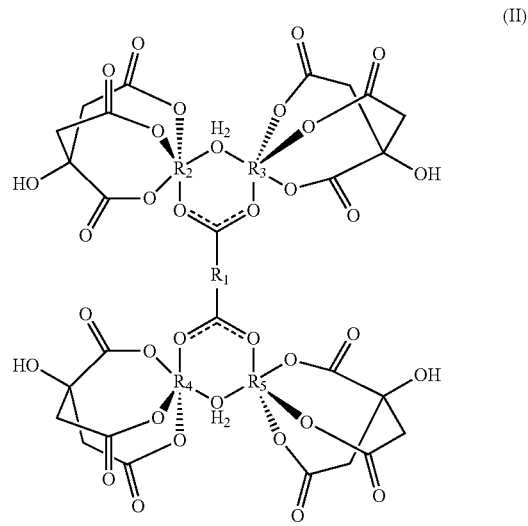

(II)

where $R_1$ is the intervening spacer and may be an alkylene group, an arylene group, an arylalkylene group, or an alkylarylene group (as defined above), and $R_2$, $R_3$, $R_4$ and $R_5$ may be the same or different polyvalent metal atom, such as a metal atom selected from the group consisting of aluminum, zirconium, and titanium. For example, in the above structure, $R_2$ and $R_5$ may be zirconium, and $R_3$ and $R_4$ may be aluminum, or $R_2$ and $R_4$ may be zirconium, and $R_3$ and $R_5$ may be aluminum.

In specific embodiments, the spread crosslinker may have an intervening spacer that is an alklyene group, such as formula III below, where n may be an integer in a range of from 1 to about 40, such as from about 4 to about 25, or about 6 to about 15:

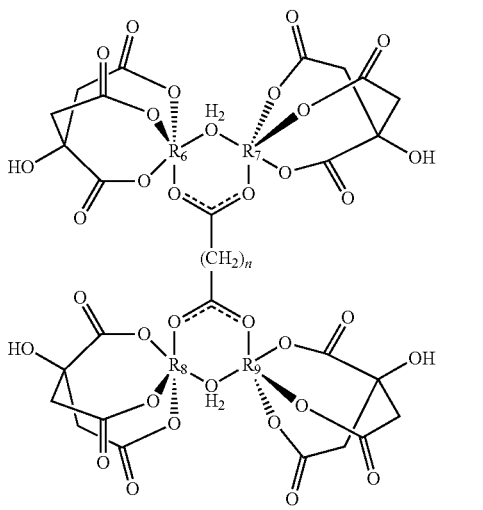

(III)

and $R_6$, $R_7$, $R_8$ and $R_9$ may be the same or different polyvalent metal atom, such as a metal atom selected from the group consisting of aluminum, zirconium, and titanium. For example, in the above structure, $R_6$ and $R_9$ may be zirconium, and $R_7$ and $R_8$ may be aluminum, or $R_6$ and $R_8$ may be zirconium, and $R_7$ and $R_9$ may be aluminum.

In embodiments, the spread crosslinker is a compound having the following general formula

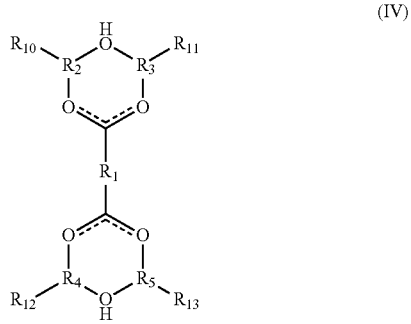

(IV)

where $R_1$ is the intervening spacer and may be an alkylene group, an arylene group, an arylalkylene group, or an alkylarylene group (as defined above); $R_2$, $R_3$, $R_4$ and $R_5$ may be the same or different polyvalent metal atom, such as a polyvalent metal atom selected from the group consisting of aluminum, zirconium, and titanium; and one or more of $R_{10}$, $R_{11}$, $R_{12}$ and $R_{13}$ represents, independent from one another, a unidentate, bidentate, tridentate, or polydentate ligand system (as discussed above). In some embodiments, two or more of $R_{10}$, $R_{11}$, $R_{12}$ and $R_{13}$ represents, independent from one another, a unidentate, bidentate, tridentate, or polydentate ligand system (as discussed above). In specific embodiments, each of $R_{10}$, $R_{11}$, $R_{12}$ and $R_{13}$ represents, independent from one another, a unidentate, bidentate, tridentate, or polydentate ligand system.

In further embodiments, each of $R_{10}$, $R_{11}$, $R_{12}$ and $R_{13}$ represents the same or different ligand system. For example, in embodiments, each of $R_{10}$, $R_{11}$, $R_{12}$ and $R_{13}$, independent from one another, may be a tridentate ligand system obtained from the reaction with a chelating agent comprising citric acid.

In embodiments, as result of the choice of the ligand system (including the chelating agent) for the spread crosslinker of the present disclosure, the rate of crosslinking may be retarded or delayed such that a gelled fluid may be readily pumped into a wellbore for entry into a subterranean formation before substantial crosslinking occurs in the crosslinkable fluid. One of ordinary skill in the art would appreciate that additional additives may be included in the crosslinkable fluid to provide additional delay before substantial crosslinking occurs in the crosslinkable fluid.

In embodiments, once the crosslinkable fluid is mixed, substantial crosslinking does not occur in the crosslinkable fluid immediately, such as for at least about 30 minutes, such as for at least about two hours, or for at least about several days. The phrase "substantial crosslinking does not occur" means that at least 80% of the crosslinkable component remains uncrosslinked once the crosslinkable fluid is mixed, such as at least 95%, or as at least 99% of the crosslinkable component remains uncrosslinked once the crosslinkable fluid is mixed.

The crosslinkable fluid of the present disclosure may be tailored by selecting appropriate chelating agents and headgroup structures and optionally other additives such that the crosslinking occurs over a desired time interval. For example, the components of the crosslinkable fluid and/or the conditions the crosslinkable fluid is exposed to may be selected such that the crosslinking occurs in less than about 0.5 hour, or selected such that the crosslinking occurs in over the course of a few hours, days or even weeks. Additionally, the components of the crosslinkable fluid and/or the conditions the crosslinkable fluid is exposed to may be selected such that the doubling of the apparent viscosity of the crosslinkable fluid may occur over about 0.5 hours to a few weeks, such as over two hours to several days. The components of the crosslinkable fluid and/or the conditions the crosslinkable fluid is exposed to may also be selected such that the apparent viscosity increases to about 50 percent of its ultimate value upon sitting for about 0.5 hours to several days at room temperature.

In embodiments, the crosslinkable fluid may further comprise an additional cross linking agent (in addition to the spread crosslinker). The phrase "cross linking agent" refers, for example, to a compound or mixture that assists in the formation of a three dimensional polymerized structure of the crosslinkable component under at least some downhole conditions. Suitable cross linking agents for the methods of the present disclosure would be capable of crosslinking polymer molecules to form a three-dimensional network. Suitable organic crosslinking agents include, but are not limited to, aldehydes, dialdehydes, phenols, substituted phenols, and ethers. Suitable inorganic crosslinking agents include, but are not limited to, polyvalent metals, conventional chelated polyvalent metals, and compounds capable of yielding polyvalent metals. The concentration of the cross linking agent (including the spread crosslinker) in the crosslinkable fluid may be from about 0.001 wt % to about 10 wt %, such as about 0.005 wt % to about 2 wt %, or about 0.01 wt % to about 1 wt %.

While the crosslinkable fluids or treatment fluids of the present disclosure are described herein as comprising the above-mentioned components, it should be understood that the crosslinkable fluids of the present disclosure may optionally comprise other chemically different materials. In embodiments, the crosslinkable fluid may further comprise stabilizing agents, surfactants, diverting agents, or other additives. Additionally, a crosslinkable fluid may comprise a mixture various other crosslinking agents, and/or other additives, such as fibers or fillers, provided that the other components chosen for the mixture are compatible with the intended use of forming a crosslinked three dimensional structure that at least partially seals a portion of a subterranean formation, such as a water bearing portion of a subterranean formation, permeated by the crosslinkable fluid or treatment fluid. In embodiments, the crosslinkable fluid of the present disclosure may further comprise one or more components selected from the group consisting of a gel breaker, a buffer, a proppant, a clay stabilizer, a gel stabilizer, a surfactant and a bactericide. Furthermore, the crosslinkable fluid or treatment fluid may comprise buffers, pH control agents, and various other additives added to promote the stability or the functionality of the fluid. The crosslinkable fluid or treatment fluid may be based on an aqueous or non-aqueous solution. The components of the crosslinkable fluid or treatment fluid may be selected such that they may or may not react with the subterranean formation that is to be sealed.

In this regard, the crosslinkable fluid or treatment fluid may include components independently selected from any solids, liquids, gases, and combinations thereof, such as slurries, gas-saturated or non-gas-saturated liquids, mixtures of two or more miscible or immiscible liquids, and the like, as long as such additional components allow for the formation of a three dimensional structure upon substantial completion of the crosslinking reaction. For example, the crosslinkable fluid or treatment fluid may comprise organic chemicals, inorganic chemicals, and any combinations thereof. Organic chemicals may be monomeric, oligomeric, polymeric, crosslinked, and combinations, while polymers may be thermoplastic, thermosetting, moisture setting, elastomeric, and the like. Inorganic chemicals may be metals, alkaline and alkaline earth chemicals, minerals, and the like. Fibrous materials may also be included in the crosslinkable fluid or treatment fluid. Suitable fibrous materials may be woven or nonwoven, and may be comprised of organic fibers, inorganic fibers, mixtures thereof and combinations thereof.

Stabilizing agents can be added to slow the degradation of the crosslinked structure after its formation downhole. Typical stabilizing agents include buffering agents, such as agents capable of buffering at pH of about 8.0 or greater (such as water-soluble bicarbonate salts, carbonate salts, phosphate salts, or mixtures thereof, among others); and chelating agents (such as ethylenediaminetetraacetic acid (EDTA), nitrilotriacetic acid (NTA), or diethylenetriaminepentaacetic acid (DTPA), hydroxyethylethylenediaminetriacetic acid (HEDTA), or hydroxyethyliminodiacetic acid (HEIDA), among others), which may or may not be the same as used for the coordinated ligand system of the chelated metal of the spread crosslinker. Buffering agents may be added to the crosslinkable fluid or treatment fluid in an amount from about 0.05 wt % to about 10 wt %, and from about 0.1 wt % to about 2 wt %, based upon the total weight of the crosslinkable fluid or treatment fluid. Additional chelating agents may be added to the crosslinkable fluid or treatment fluid to at least about 0.75 mole per mole of metal ions expected to be encountered in the downhole environment, such as at least about 0.9 mole per mole of metal ions, based upon the total weight of the crosslinkable fluid or treatment fluid.

Surfactants can be added to promote dispersion or emulsification of components of the crosslinkable fluid, or to provide foaming of the crosslinked component upon its formation downhole. Suitable surfactants include alkyl polyethylene oxide sulfates, alkyl alkylolamine sulfates, modified ether alcohol sulfate sodium salts, or sodium lauryl sulfate, among others. Any surfactant which aids the dispersion and/or stabilization of a gas component in the fluid to form an energized fluid can be used. Viscoelastic surfactants, such as those described in U.S. Pat. Nos. 6,703,352, 6,239,183, 6,506,710, 7,303,018 and 6,482,866, each of which are incorporated by reference herein in their entirety, are also suitable for use in fluids in some embodiments. Examples of suitable surfactants also include, but are not limited to, amphoteric surfactants or zwitterionic surfactants. Alkyl betaines, alkyl amido betaines, alkyl imidazolines, alkyl amine oxides and alkyl quaternary ammonium carboxylates are some examples of zwitterionic surfactants. An example of a useful surfactant is the amphoteric alkyl amine contained in the surfactant solution AQUAT 944® (available from Baker Petrolite of Sugar Land, Tex.). A surfactant may be added to the crosslinkable fluid in an amount in the range of about 0.01 wt % to about 10 wt %, such as about 0.1 wt % to about 2 wt %.

Charge screening surfactants may be employed. In some embodiments, the anionic surfactants such as alkyl carboxylates, alkyl ether carboxylates, alkyl sulfates, alkyl ether sulfates, alkyl sulfonates, α-olefin sulfonates, alkyl ether sulfates, alkyl phosphates and alkyl ether phosphates may be used. Anionic surfactants have a negatively charged moiety and a hydrophobic or aliphatic tail, and can be used to charge screen cationic polymers. Examples of suitable ionic surfactants also include, but are not limited to, cationic surfactants such as alkyl amines, alkyl diamines, alkyl ether amines, alkyl quaternary ammonium, dialkyl quaternary ammonium and ester quaternary ammonium compounds. Cationic surfactants have a positively charged moiety and a hydrophobic or aliphatic tail, and can be used to charge screen anionic polymers such as CMHPG.

In other embodiments, the surfactant is a blend of two or more of the surfactants described above, or a blend of any of the surfactant or surfactants described above with one or more nonionic surfactants. Examples of suitable nonionic surfactants include, but are not limited to, alkyl alcohol ethoxylates, alkyl phenol ethoxylates, alkyl acid ethoxylates, alkyl amine ethoxylates, sorbitan alkanoates and ethoxylated sorbitan alkanoates. Any effective amount of surfactant or blend of surfactants may be used in aqueous energized fluids.

Friction reducers may also be incorporated in any fluid embodiment. Any suitable friction reducer polymer, such as polyacrylamide and copolymers, partially hydrolyzed polyacrylamide, poly(2-acrylamido-2-methyl-1-propane sulfonic acid) (polyAMPS), and polyethylene oxide may be used. Commercial drag reducing chemicals such as those sold by Conoco Inc. under the trademark "CDR" as described in U.S. Pat. No. 3,692,676 or drag reducers such as those sold by Chemlink designated under the trademarks FLO1003, FLO1004, FLO1005 and FLO1008 have also been found to be effective. These polymeric species added as friction reducers or viscosity index improvers may also act as excellent fluid loss additives reducing or even eliminating the use of conventional fluid loss additives. Latex resins or polymer emulsions may be incorporated as fluid loss additives. Shear recovery agents may also be used in embodiments.

Diverting agents may be added to improve penetration of the crosslinkable fluid into lower-permeability areas when treating a zone with heterogeneous permeability. The use of diverting agents in formation treatment applications is known, such as given in Reservoir Stimulation, $3^{rd}$ edition, M. Economides and K. Nolte, eds., Section 19.3.

In embodiments, the components of the crosslinkable fluid may be selected so that the morphology of the crosslinked structure, which forms by crosslinking the crosslinkable fluid, may be tuned to provide the desired sealing function. Such morphologies of the crosslinked fluid system may include, for example, a gelled material such as an elastic gel, a rigid gel, etc.; a slurried material; an elastic solid; a rigid solid; a brittle solid; a foamed material, and the like. In embodiments, the components of the crosslinkable fluid may be selected such that a crosslinking reaction substantially occurs at a temperature above the bottom hole static temperature (BHST), such as at least 20° C. above BHST, or at least 50° C. above BHST.

The crosslinkable fluid for treating a subterranean formation of the present disclosure may be a fluid that has a viscosity of above about 50 centipoise at 100 sec$^{-1}$, such as a viscosity of above about 100 centipoise at 100 sec$^{-1}$ at the treating temperature, which may range from a surface temperature to a bottom-hole static (reservoir) temperature, such as from about 4° C. to about 80° C., or from about 10° C. to about 70° C., or from about 25° C. to about 60° C., or from about 32° C. to about 55° C. In embodiments, the crosslinked structure formed may be a gel that is substantially non-rigid after substantial crosslinking. In some embodiments, crosslinked structure formed is a non-rigid gel may substantially return to its starting condition after compression with a linear strain of at least about 10%, such as at least about 25%, or greater than about 50%. Non-rigidity of which can be determined by any techniques known to those of ordinary skill in the art. The storage modulus G' of substantially crosslinked fluid system of the present disclosure, as measured according to standard protocols given in U.S. Pat. No. 6,011,075, the disclosure of which is hereby incorporated by reference in its entirety, may be about 150 dynes/cm$^2$ to about 500,000 dynes/cm$^2$, such as from about 1000 dynes/cm$^2$ to about 200,000 dynes/cm$^2$, or from about 10,000 dynes/cm$^2$ to about 150,000 dynes/cm$^2$.

After the crosslinkable fluid is prepared, it can be injected or conveyed into a subterranean formation to substantially seal at least a portion of the subterranean formation upon polymerization of one or more of the components of the crosslinkable fluid (by exposure to electromagnetic radiation). In embodiments, at least some of the crosslinkable fluid permeates a portion of the subterranean formation, such as a water-bearing subterranean formation.

In embodiments, the crosslinkable components are not substantially crosslinked under the subterranean conditions (downhole conditions) until the crosslinkable fluid is introduced into the desired location. In other words, the crosslinking reaction between the spread crosslinking agent and the crosslinkable component does not substantially occur until the crosslinkable fluid is downhole. For example, at least 80% of the crosslinkable component remains uncrosslinked (under the conditions experienced downhole) until the crosslinkable fluid is positioned in the desired location in the wellbore in the vicinity of the subterranean formation to be sealed, such as at least 95%, or as at least 99% of the crosslinkable component remains uncrosslinked (under the conditions experienced downhole) until the crosslinkable fluid is positioned in the desired location in the wellbore in the vicinity of the subterranean formation to be sealed.

In embodiments, the crosslinkable fluid systems are introduced into the subterranean material surrounding a wellbore by flowing the crosslinkable fluid system into the wellbore. A "wellbore" may be any type of well, including, but not limited to, a producing well, a non-producing well, an injection well, a fluid disposal well, an experimental well, an exploratory well, and the like. Wellbores may be vertical, horizontal, deviated some angle between vertical and horizontal, and combinations thereof, for example a vertical well with a non-vertical component. In embodiments, the one or more crosslinkable components of the crosslinkable fluid does not crosslink until after its introduction into the wellbore, such as injection and/or permeation into the subterranean formation.

In embodiments, the crosslinked composition that is formed following the crosslinking reaction at least partially seals, and may completely seal, at least a portion of a subterranean formation through which crosslinkable fluid systems are dispersed. For example, crosslinking the crosslinkable fluid of the present disclosure may be conducted such that the permeability of the subterranean formation substantially decreases. In embodiments, after crosslinking the crosslinkable fluid of the present disclosure, the permeability of the subterranean formation, such as a water bearing subterranean formation, may decrease by at least about 80%, such as at least about 90%, or by at least about 99%.

Fluids may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. In the case of borate-crosslinked gels, increasing the pH and therefore increasing the effective concentration of the active crosslinker, the borate anion, reversibly create the borate crosslinks. Lowering the pH can just as easily remove the borate/polymer bonds. At a high pH above 8, the borate ion exists and is available to crosslink and cause gelling. At lower pH, the borate is tied up by hydrogen and is not available for crosslinking, thus gelation by borate ion is reversible.

Embodiments may also include proppant particles that are substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it may be from about 20 to about 100 U.S. Standard Mesh in size. With synthetic proppants, mesh sizes about 8 or greater may be used. Naturally occurring materials may be underived and/or unprocessed naturally occurring materials, as well as materials based on naturally occurring materials that have been processed and/or derived. Suitable examples of naturally occurring particulate materials for use as proppants include: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particulation, processing, etc. Further information on nuts and composition thereof may be found in ENCYCLOPEDIA OF CHEMICAL TECHNOLOGY, Edited by Raymond E. Kirk and Donald F. Othmer, Third Edition, John Wiley & Sons, vol. 16, pp. 248-273, (1981).

The concentration of proppant in the fluid can be any concentration known in the art. For example, the concentration of proppant in the fluid may be in the range of from about 0.03 to about 3 kilograms of proppant added per liter of liquid phase. Also, any of the proppant particles can further be coated with a resin to potentially improve the strength, clustering ability, and flow back properties of the proppant.

A fiber component may be included in the fluids to achieve a variety of properties including improving particle suspension, and particle transport capabilities, and gas phase stability. Fibers used may be hydrophilic or hydrophobic in nature. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON® polyethylene terephthalate (PET) Fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids, the fiber component may be included at concentrations from about 1 to about 15 grams per liter of the liquid phase of the fluid, such as a concentration of fibers from about 2 to about 12 grams per liter of liquid, or from about 2 to about 10 grams per liter of liquid.

Embodiments may further use fluids containing other additives and chemicals that are known to be commonly used in oilfield applications by those skilled in the art. These include, but are not necessarily limited to, materials such as surfactants in addition to those mentioned hereinabove, breaker aids in addition to those mentioned hereinabove, oxygen scavengers, alcohol stabilizers, scale inhibitors, corrosion inhibitors, fluid-loss additives, bactericides and biocides such as 2,2-dibromo-3-nitrilopropionamine or glutaraldehyde, and the like. Also, they may include a co-surfactant to optimize viscosity or to minimize the formation of stable emulsions that contain components of crude oil.

As used herein, the term "alcohol stabilizer" is used in reference to a certain group of organic molecules substantially or completely soluble in water containing at least one hydroxyl group, which are susceptible of providing thermal stability and long term shelf life stability to aqueous zirconium complexes. Examples of organic molecules referred as "alcohol stabilizers" include but are not limited to methanol, ethanol, n-propanol, isopropanol, n-butanol, tert-butanol, ethyleneglycol monomethyl ether, and the like.

In the methods of the present disclosure, crosslinking the crosslinkable fluid may also comprise applying an electromagnetic radiation, such as a microwave, optionally in combination with one or more other techniques, such as mechanical, physical, chemical, thermal initiation, and the like. For example, the methods of the present disclosure may comprise flowing one or more crosslinkable fluid systems into a subterranean material to be sealed, such as a subterranean formation immediately adjacent to a wellbore, and crosslinking one or more of the components of the crosslinkable fluid by exposing the crosslinkable fluid to an effective amount, such as, for example, from about 200 W to about 2000 W, from about 500 W to about 1500 W and from about 750 W to about 1000 W, of electromagnetic radiation (produced by an electromagnetic radiation source placed in close proximity to the medium to be sealed) suitable to crosslink one or more of the components of the crosslinkable fluid system, thereby effectively sealing the material occupied by the crosslinkable fluid.

Methods of the present disclosure may be used to seal or reduce the flow of an unacceptable amount of water (or other undesired material) into or near the wellbore. The phrase unacceptable amount of water (or other undesired material) may be determined on a case-by-case basis. As used herein, the terms "seal", "sealed" and "sealing" mean at least the ability to substantially prevent fluids, such as fluids comprising an unacceptable amount of water, to flow through the area where the crosslinkable components of the crosslinkable fluid were crosslinked. The terms "seal", "sealed" and "sealing" may also mean the ability to substantially prevent fluids from flowing between the medium where the crosslinkable components of the crosslinkable fluid were crosslinked and whatever surface it is sealing against, for example an open hole, a sand face, a casing pipe, and the like.

After at least a portion of the crosslinkable fluid has permeated the subterranean formation, such as water-bearing subterranean formation, the methods of the present disclosure may comprise crosslinking the crosslinkable components of the crosslinkable fluid to form a three dimensional crosslinked structure and seal the subterranean formation. As discussed above, a subterranean formation is sealed if part or a majority of subterranean formation has been treated with the crosslinkable fluid and the crosslinkable components of the crosslinkable fluid in this treated zone have been crosslinked in a sufficient amount such that the permeability of the subterranean formation is reduced. For example, upon formation of a three dimensional crosslinked structure as a result of crosslinking the crosslinkable components of the crosslinkable fluid of the present disclosure, the permeability of the subterranean formation may decrease by at least about 80%, such as by at least about 90%, or by at least about 99%. In embodiments, for a predetermined vertical region (depending on the vertical depth of the region to be sealed), the sealed zone may be a volume extending at least about 15 cm from the outer wall of the wellbore, such as a volume extending at least about 30 cm from the outer wall of the wellbore, or a volume extending at least about 50 cm from the outer wall of the wellbore.

In the methods of the present disclosure, crosslinking may be accomplished by exposing the crosslinkable fluid to heat and/or electromagnetic radiation to generate a thermal reaction. In embodiments, the crosslinking may be substantially completed, such as about 75% of spread crosslinker is reacted, or about 95% of spread crosslinker is reacted, or about 99.9% of spread crosslinker is reacted, in a time no less than about 0.5 hours, or in a time no less than about one day, such as a time no less than about two weeks.

In some embodiments, the crosslinking temperature may be set such that a permanent crosslink, such as a crosslinked material formed from a spread crosslinker comprising Zr or Ti, is completed in the lower portion of the wellbore or after exiting the perforations into the fracture. This will minimize the damage done by high shear experienced during tubular transit. For example, the crosslinking temperature may be set at a temperature in the range of from 5° C. to about 40° C., such as a temperature in the range of from 10° C. to about 30° C.

Methods of the present disclosure may include those where the energy sufficient to bring about a thermal reaction is supplied in the form of electromagnetic radiation that is generated by an electromagnetic radiation source that is positioned in the wellbore. Known sources (such as lamps, antennas, etc.,) for producing the desired form of electromagnetic radiation may be used with the methods of the present disclosure as long as they are designed to be able to withstand the downhole environment. The electromagnetic radiation source may be inserted into the wellbore either before or after conveying a crosslinkable fluid to the subterranean formation to be sealed via a suitable delivery method, such as coiled tubing. In embodiments, the electromagnetic radiation source may be positioned with or without a communication line, such as a slickline, micro-line, or micro-wire. In embodiments, the electromagnetic radiation source may accompany the coiled tubing, either attached to the outside of the coiled tubing, or disposed inside the coiled tubing. Then, after the crosslinkable fluid has sufficiently penetrated the medium to be sealed, the electromagnetic radiation source may be used to generate electromagnetic radiation, such as microwave or other radio-frequencies, to accelerate the crosslinking reaction of one or more components of the crosslinkable fluid to completion.

An electromagnetic radiation source may be any unit capable of transmitting electromagnetic energy to the crosslinkable fluid, such as, for example, a wireline tool.

In embodiments, a sensor may be attached to a distal end of a communication line that is inserted into the wellbore and data may be collected and used to monitor status of the crosslinking reaction, or model subsequent applications of triggering conditions. The measured property for monitoring the progress of the crosslinking reaction at or near the medium to be sealed may be any property that may be measured downhole that provides an indication that the crosslinking reaction is proceeding, including but not limited to, temperature, pH, amount of precipitate, fluid temperature, depth, presence of water, chemical luminescence, gamma-ray, resistivity, salinity, fluid flow, fluid compressibility, electromagnetic trigger unit location, electromagnetic trigger unit state and electromagnetic trigger unit orientation. In particular embodiments, the parameter being measured may be any parameter that may be adjusted, including but not limited to quantity of crosslinkable component in the crosslinkable fluid, relative proportions of each component in the crosslinkable fluid, the chemical concentration of one or more components in a set of crosslinkable fluids, the relative proportion of fluids being pumped in the annulus to fluids being pumped in the coiled tubing, concentration of the spread crosslinker, concentration of other optional components, and/or location of coiled tubing.

The crosslinkable fluids of the present disclosure may be suitable for use in numerous subterranean formation types. For example, formations for which sealing with the crosslinkable fluids of the present disclosure may be used include sand, sandstone, shale, chalk, limestone, and any other hydrocarbon bearing formation.

The portion of the wellbore through which the crosslinkable fluid is injected into the treated zone can be open-hole (or comprise no casing) or can have previously received a casing. If cased, the casing is desirably perforated prior to injection of the crosslinkable fluid. Optionally, the wellbore can have previously received a screen. If it has received a screen, the wellbore can also have previously received a gravel pack, with the placing of the gravel pack optionally occurring above the formation fracture pressure (a frac-pack).

Techniques for injection of fluids with viscosities similar to those of the crosslinkable fluids of the present disclosure are well known in the art and may be employed with the methods of the present disclosure. For example, known techniques may be used in the methods of the present disclosure to convey the crosslinkable fluids of the present disclosure into the subterranean formation to be treated.

In embodiments, the crosslinkable fluid may be driven into a wellbore by a pumping system that pumps one or more crosslinkable fluids into the wellbore. The pumping systems may include mixing or combining devices, wherein various components, such as fluids, solids, and/or gases maybe mixed or combined prior to being pumped into the wellbore. The mixing or combining device may be controlled in a number of ways, including, but not limited to, using data obtained either downhole from the wellbore, surface data, or some combination thereof. Methods of this disclosure may include using a surface data acquisition and/or analysis system, such as described in U.S. Pat. No. 6,498,988, incorporated herein by reference in its entirety. In embodiments, one or more crosslinkable fluid is pumped into the wellbore after detecting an unacceptable amount of water or other condition has been detected. Specific embodiments may comprise sealing the zone of interest (which may be where an unacceptable amount of water or other condition has been detected) using the crosslinkable fluid optionally with packers, such as straddle cup packers. Packers or similar devices can be used to control flow of the crosslinkable fluid into the subterranean formation for which sealing is desired.

In embodiments, the crosslinkable fluid may be injected into the subterranean formation at a pressure less than the fracturing pressure of the formation. For example, the crosslinkable fluids will be injected below the formation fracturing pressure of the respective formation.

The volume of crosslinkable fluids to be injected into subterranean formation is a function of the subterranean formation volume to be treated and the ability of the crosslinkable fluid of the present disclosure to penetrate the subterranean formation. The volume of crosslinkable fluid to be injected can be readily determined by one of ordinary skill in the art. As a guideline, the formation volume to be treated relates to the height of the desired treated zone and the desired depth of penetration. In embodiments, the depth of penetration of the crosslinkable fluid may be at least about 15 cm from the outer wall of the wellbore into the subterranean formation, such as the depth of penetration of at least about 30 cm from the outer wall of the wellbore.

The ability of the crosslinkable fluid to penetrate the subterranean formation depends on the permeability of the subterranean formation and the viscosity of the crosslinkable fluid. In embodiments, the viscosity of the crosslinkable fluid is sufficiently low as to not slow penetration of the consolidating fluid into the subterranean formation. In a low-permeability subterranean formation, the viscosity of the crosslinkable fluid is sufficiently low as to not slow penetration of the consolidating fluid into the subterranean formation. For example, in a low-permeability subterranean formation, suitable initial viscosities may be similar to that of water, such as from about from about 1 cP to about 10,000 cP, or be from about 1 cP to about 1,000 cP, or be from about 1 cP to about 100 cP at the treating temperature, which may range from a surface temperature to a bottom-hole static (reservoir) temperature, such as from about 4° C. to about 80° C., or from about 10° C. to about 70° C., or from about 25° C. to about 60° C., or from about 32° C. to about 55° C.

In embodiments, after the crosslinkable fluid penetrates the subterranean formation, the crosslinking reaction occurs, whereby the one or more the components of the crosslinkable fluid, including the spread crosslinker are crosslinked. The crosslinked structure formed may comprise three-dimensional linkages that effectively blocks permeation of fluids through the sealed region. Thus, the sealed subterranean formation becomes relatively impermeable and any remaining pores in the sealed subterranean formation do not communicate with the wellbore and do not produce water.

After the subterranean formation has been sealed according to the methods of the present disclosure, it may be rendered relatively impermeable. In embodiments, the permeability of the subterranean formation may be reduced by at least about 90%, such as by at least about 95%, or by at least about 99%. In embodiments, fracturing or perforating through the sealed subterranean formation may be performed to allow communication through the sealed subterranean formation.

The fluids and/or methods may be used for hydraulically fracturing a subterranean formation. Techniques for hydraulically fracturing a subterranean formation are known to persons of ordinary skill in the art, and involve pumping a fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications," Encyclopedia of Polymer Science and Engineering, vol. 10, pp. 328-366 (John Wiley & Sons, Inc. New York, N.Y., 1987) and references cited therein.

In various embodiments, hydraulic fracturing involves pumping a proppant-free viscous fluid, or pad—such as water with some fluid additives to generate high viscosity—into a well faster than the fluid can escape into the formation so that the pressure rises and the rock breaks, creating artificial fractures and/or enlarging existing fractures. Then, proppant particles are added to the fluid to form slurry that is pumped into the fracture to prevent it from closing when the pumping pressure is released. In the fracturing treatment, fluids of are used in the pad treatment, the proppant stage, or both.

The foregoing may be better understood by reference to the following examples, which are presented for purposes of illustration and are not intended to limit the scope of the present disclosure.

EXAMPLES

Initially, a 0.42 weight percent solution of hydroxypropyl guar (HPG) was hydrated using a Waring blender in synthetic seawater made with Instant Ocean sea salt and deionized water.

Example 1

(Modification of a dual-headgroup zirconium/aluminum compound with citric acid): 0.29 grams of citric acid were dissolved into 3 grams of a dual-headgroup compound containing zirconium and aluminum having the following structure:

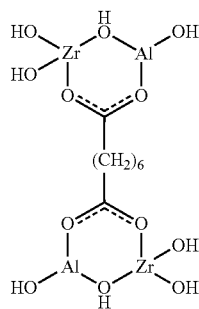

This resulted in a clear solution containing a modified dual-headgroup zirconium/aluminum compound that was chelated. To the initial 0.42% weight percent solution of HPG were added 0.3 volume percent of 10% sodium hydroxide solution, and 0.3 volume percent of the modified dual-headgroup zirconium/aluminum compound. This resulted in a visco-elastic gel. Thirty milliliters of this solution was added to the cup of a rheometer and the viscosity was tested at 100 $sec^{-1}$ while the rheometer heated to and was held at 121° C. This rheometer, a Grace Instrument model M5500, employed test geometry that complies with ISO procedure 13503-1. The results of this test and the tests for Comparative Examples 1-3 (described below) are shown in FIG. 1.

Example 2

Figure 2:
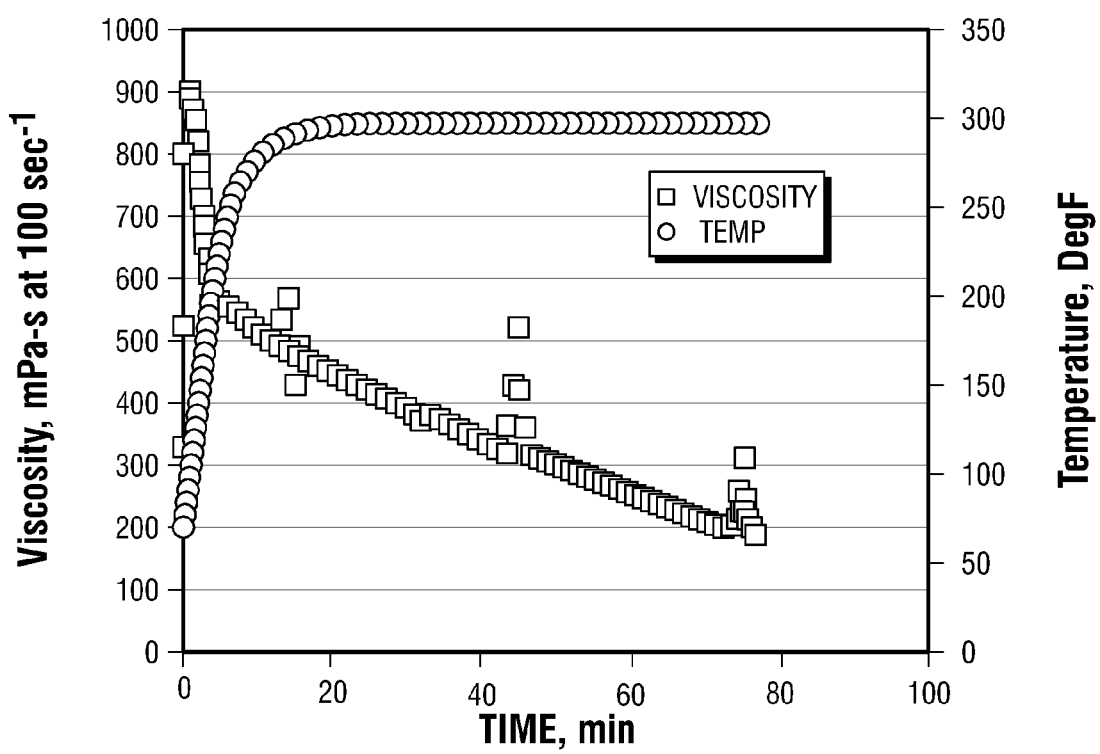
FIG. 2 is an illustration of the rheology profile of the solution prepared in Example 2.

A 0.54 weight percent solution of hydroxypropyl guar (HPG) was prepared in synthetic seawater, similar to the HPG solution used in Example 1. To this, 0.24 weight percent of sodium thiosulfate, 0.025 volume percent of a 30% potassium carbonate solution, and 0.1 volume percent of the dual-headgroup zirconium/aluminum compound from Example 3 were added, giving a gel with pH 8.9. Thirty milliliters of this gel was added to the rheometer cup, and again tested in the same fashion as Example 1, except the temperature was held at 149° C. The results of this test are shown in FIG. 2.

Example 3

Figure 3:
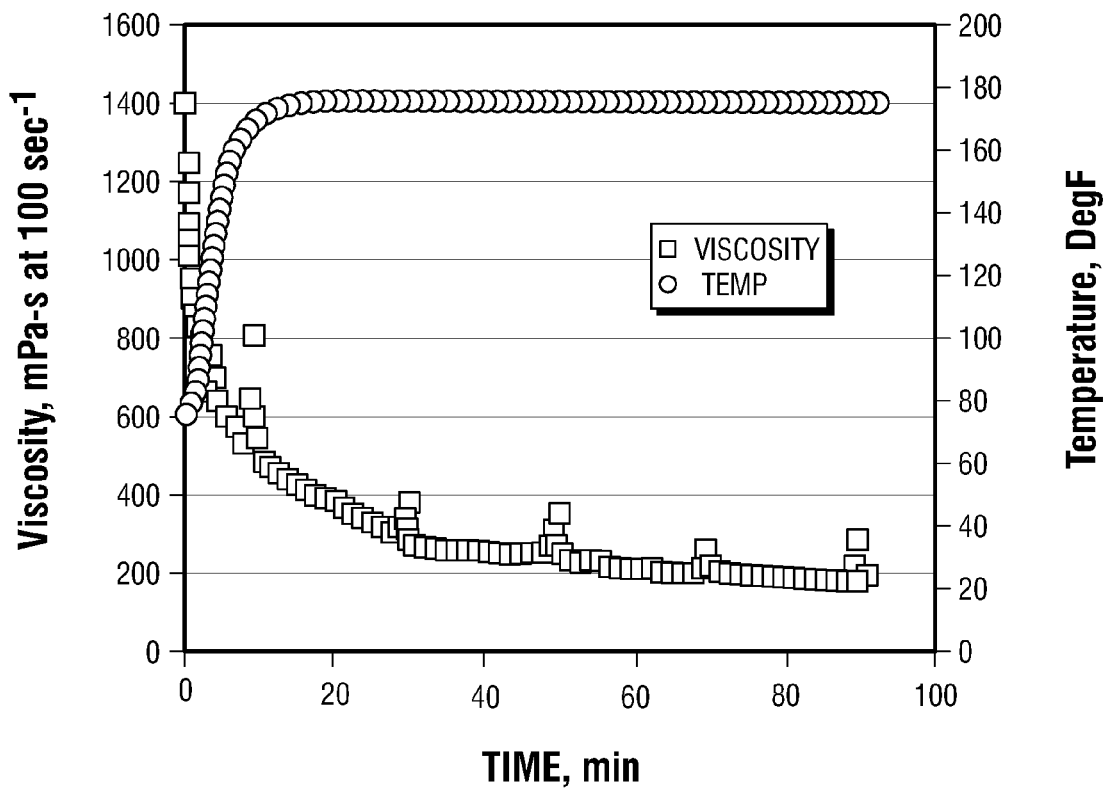
FIG. 3 is an illustration of the rheology profile of the solution prepared in Example 3.

A 0.48% solution of guar was prepared and hydrated as above in deionized water. To this, 0.12 weight percent sodium thiosulfate and 0.15 volume percent of a 10% sodium hydroxide were added. 0.05 volume percent of the modified dual-headgroup zirconium/aluminum compound was added. The resulting, strongly gelled polymer was tested similarly to Example 2 on the rheometer. The results of this test are shown in FIG. 3. The high initial viscosity and viscosity persistence at temperature confirm crosslinking with guar.

Example 4

Figure 4:
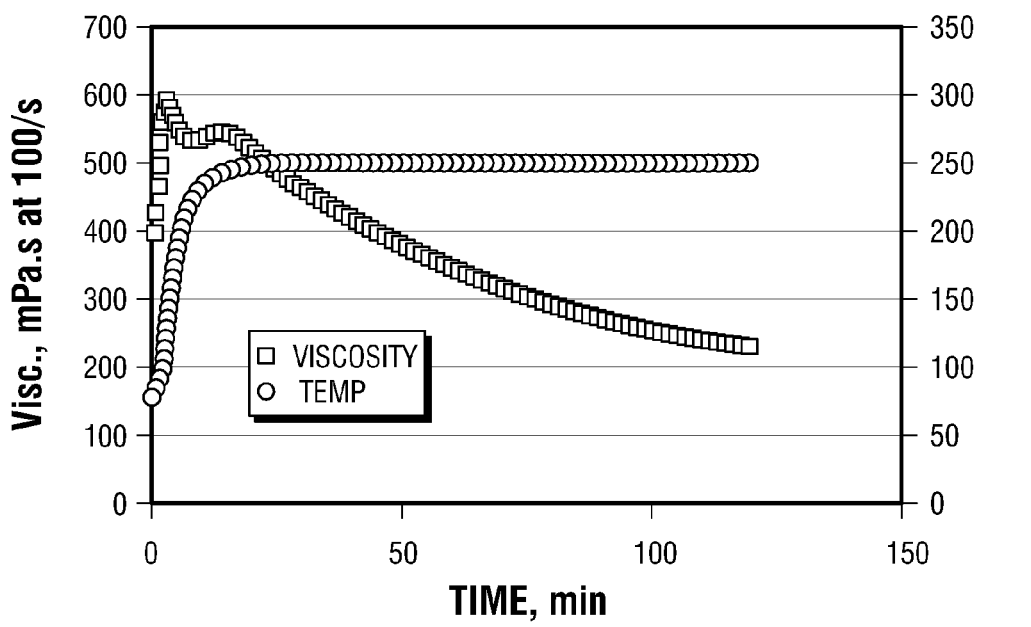
FIG. 4 is an illustration of the rheology profile of the solution prepared in Example 4.

A synthetic seawater was made by dissolving 36 grams of an aquarium salt, Instant Ocean, into 1 liter of deionized water. 4.2 grams/liter hydroxypropyl guar (HPG) was added to the synthetic seawater and buffered with an acetic acid/acetate mixture to a pH of about 7. This buffered solution was hydrated in the synthetic seawater using a Waring blender. The pH of the hydrated solution was raised with 0.15 volume percent of a 10 weight percent solution of sodium hydroxide, followed by introduction of 0.05% volume percent of the modified dual-headgroup zirconium/aluminum compound. The sample, which had a final pH of about 9, was loaded onto the rheometer, and tested at 121° C. The results of this test are shown in FIG. 4. This example shows a viable fracturing gel produced in a synthetic seawater, stable at temperature.

Furthermore, no evidence of scaling deposits on the rheometer parts were noted when the fluid of Example 4 was removed. Scaling in seawater (and other brines containing divalent along with carbonates/bicarbonates) may occur at a pH above about 9.5. Such information may be used to demonstrate that a stable fluid with the composition of Example 4 and containing seawater does not indicate scaling, and will therefore leave the proppant pack conductive to fluids. Borate-containing fluids are generally not used with seawater for high temperatures, as they require a pH which may result in the precipitation of scale (i.e., calcite, magnesite and hydroxide) that impair conductivity.

Comparative Example 1

To the above viscous HPG solution of 0.42 weight percent solution, 0.03 volume percent of a 10% sodium hydroxide solution was introduced (the resulting pH was 9.0). Thirty milliliters of this solution was added to the cup of a rheometer and the viscosity was tested similar to Example 1 at 100 sec$^{-1}$ while the rheometer heated to and was held at 121° C. The results of this test are shown in FIG. 1.

Comparative Example 2

To the same initially prepared hydrated HPG solution, 0.3 volume percent of 10% sodium hydroxide solution, and 0.3 volume percent of a carboxyl/hydroxyl functional organometallic zirconium/aluminum complex agent having a single ring structure was added (the resulting pH was 9.0). No viscosification was observed in the blender. As with Example 1, 30 milliliters were added to the rheometer cup and tested in the same fashion at 121° C. The results of this test are shown in FIG. 1.

Comparative Example 3

To the same initially prepared hydrated HPG solution, 0.3 volume percent of 10% sodium hydroxide solution, and 0.3 volume percent of a dual-headgroup compound containing zirconium and aluminum (non-chelated) having the following structure:

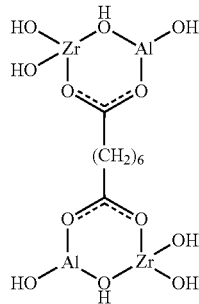

was added to the solution while mixing in the Waring blender, resulting in a pH of 9.0. Small white chips and gel strings were noted in the solution, suggesting a very rapid and localized crosslinking reaction with the polymer. As with Example 1, 30 milliliters were added to the rheometer cup and tested in the same fashion at 121° C. (as described above). The results of this test are shown in FIG. 1.

Comparative Example 4

(Modification of a carboxyl/hydroxyl functional organometallic zirconium/aluminum complex agent having a single ring structure with citric acid): 0.3 grams of citric acid were dissolved into a solution of 3 grams of a carboxyl/hydroxyl functional organometallic zirconium/aluminum complex agent having a single ring structure. This resulted in a solution containing a single headed modified zirconium/aluminum compound that was chelated.

Figure 5:
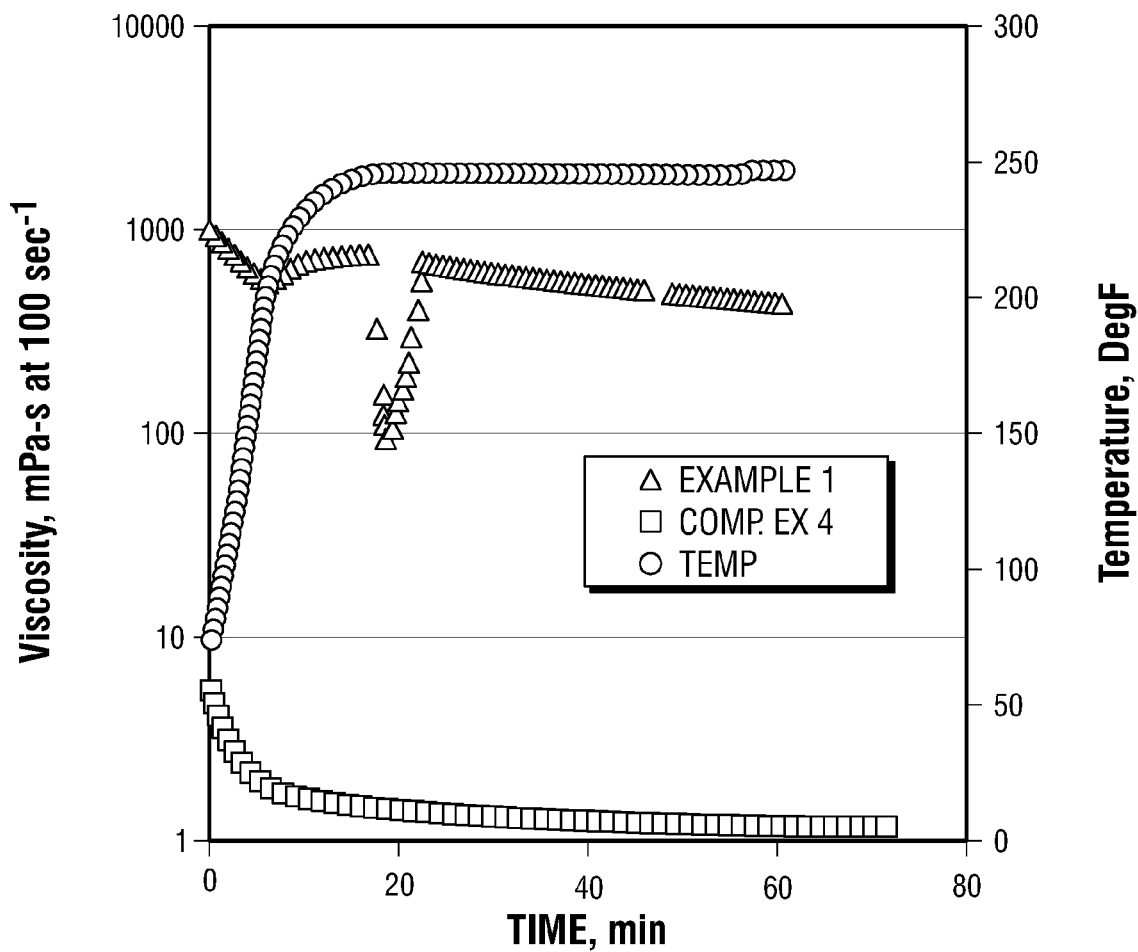
FIG. 5 is an illustration of the rheology profile of the solutions prepared in Example 1 and Comparative Example 4.

Similar to Example 4, a synthetic seawater was made by dissolving an aquarium salt, Instant Ocean, into deionized water. 4.2 grams/liter hydroxypropyl guar (HPG) was added to the synthetic seawater and buffered with an acetic acid/acetate mixture to a pH of about 7. This buffered solution was hydrated in the synthetic seawater using a Waring blender. To this solution was added a 0.12% sodium thiosulfate pentahydrate stabilizer, 0.3 volume percent of a 10 weight percent solution of sodium hydroxide, and 0.3 volume percent of the single headed modified zirconium/aluminum compound that was chelated, resulting in a solution with a pH of about 9.6. This solution was placed on the rheometer and tested as set forth above as above. The results of this test are shown in FIG. 5.

The viscosity data (shown in FIG. 1) of the fluids prepared in Example 1 and Comparative Examples 1-3 reveal that Comparative Examples 2 and 3 generate no substantial viscosity difference relative to that of Comparative Example 1, which contains no zirconium/aluminum compound. In contrast, reacting the dual-headgroup zirconium/aluminum compound used in Comparative Example 3 with citric acid to form the chelated structure resulted in a fracturing fluid with thermally-stable viscosity.

Although only a few example embodiments have been described in detail above, those skilled in the art will readily appreciate that many modifications are possible in the example embodiments without materially departing from SPREAD CROSSLINKER AND METHOD OF WATER CONTROL DOWNHOLE. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A fluid for treating a subterranean formation comprising:
   a solvent;
   a crosslinkable component; and
   a crosslinking composition comprising a spread crosslinker, the spread crosslinker having a first and a second headgroup separated by an intervening spacer that is covalently bound to the first and second headgroups, wherein
      the first headgroup comprises at least one ring of at least five atoms, where at least two of the atoms in the at least one ring of the first headgroup are chelated polyvalent metal atoms, and
      the second headgroup comprises at least one ring of at least five atoms, where at least two of the atoms in the at least one ring of the second headgroup are chelated polyvalent metal atoms.

2. The fluid for treating a subterranean formation of claim 1, wherein the at least two chelated polyvalent metal atoms of the first headgroup are
   the same or different, and
   selected from the group consisting of aluminum, zirconium, and titanium.

3. The fluid for treating a subterranean formation of claim 1, wherein the at least two chelated polyvalent metal atoms of the second headgroup are
   the same or different, and
   selected from the group consisting of aluminum, zirconium, and titanium.

4. The fluid for treating a subterranean formation of claim 1, wherein the intervening spacer is:
   an alkylene group having 1 to about 40 carbon atoms;
   an arylene group having about 5 to about 40 carbon atoms;
   an arylalkylene group having about 6 to about 40 carbon atoms; or an alkylarylene group having about 6 to about 40 carbon atoms.

5. The fluid for treating a subterranean formation of claim 1, wherein
the first headgroup contains two or more rings with each ring containing five, six, or seven atoms; and/or
the second headgroup contains two or more rings with each ring containing five, six, or seven atoms.

6. The fluid for treating a subterranean formation of claim 1, wherein
the chelated polyvalent metal atoms of the first headgroup are coordinated to a bidentate organic group or tridentate organic group, and/or
the chelated polyvalent metal atoms of the second headgroup are coordinated a bidentate organic group or tridentate organic group.

7. The fluid for treating a subterranean formation of claim 1, wherein the spread crosslinker comprises one or more compounds derived from a reaction of one or more chelating agents with a compound of formula I:

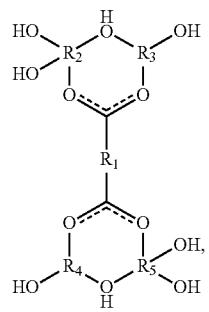

(I)

where
$R_1$ is:
an alkylene group having 1 to about 40 carbon atoms,
an arylene group having about 5 to about 40 carbon atoms,
an arylalkylene group having about 6 to about 40 carbon atoms, or
an alkylarylene group having about 6 to about 40 carbon atoms; and
$R_2$, $R_3$, $R_4$ and $R_5$ may be the same or different, and are selected from the group consisting of aluminum, zirconium, and titanium.

8. The fluid for treating a subterranean formation of claim 7, wherein the one or more chelating agent is selected from the group consisting of carboxylic acids, aminocarboxylic acids, polyols, alkanolamines, glutamic acid, lactic acid, triethanolamine, alanine, aspartic acid, oxalic acid, acetylacetonate, fumaric acid, bis-hydroxyethylglycine, maleic acid, tartaric acid, citric acid, nitrilotriacetic acid, hydroxyethyliminodiacetic acid, hydroxyethylethylenediaminetetraacetic acid, ethylenediaminetetraacetic acid, cyclohexylenediaminetetraacetic acid, diethylenetriaminepentaacetic, hydroxyethylethylenediaminetriacetic acid, diethylenetriaminepentaacetic acid, propylenediaminetetraacetic acid, ethylenediamined(o-hydroxyphenylacetic) acid, ammonium salts thereof, lithium salts thereof, sodium salts thereof, and mixtures thereof.

9. The fluid for treating a subterranean formation of claim 1, wherein the spread crosslinker comprises one or more compounds derived from a reaction of one or more chelating agents with a compound of formula II:

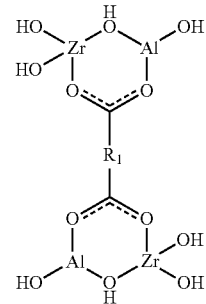

(II)

where $R_1$ is:
an alkylene group having 1 to about 40 carbon atoms,
an arylene group having about 5 to about 40 carbon atoms,
an arylalkylene group having about 6 to about 40 carbon atoms, or
an alkylarylene group having about 6 to about 40 carbon atoms.

10. The fluid for treating a subterranean formation of claim 1, wherein the spread crosslinker comprises a compound of formula III:

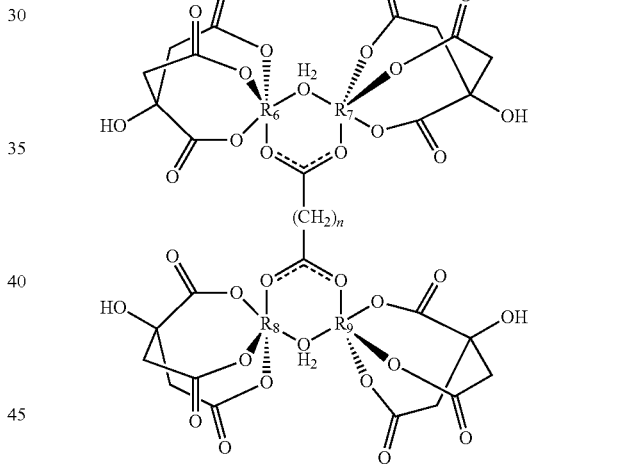

(III)

where n is an integer from 1 to about 40; and $R_6$, $R_7$, $R_8$ and $R_9$ may be the same or different, and are selected from the group consisting of aluminum, zirconium, and titanium.

11. The fluid for treating a subterranean formation of claim 1, wherein the crosslinkable component comprises a guar gum, a locust bean gum, a tara gum, a honey locust gum, a tamarind gum, a karaya gum, an arabic gum, a ghatti gum, a tragacanth gum, a carrageenen, a succinoglycan, a xanthan, a diutan, a hydroxylethylguar hydroxypropyl guar, a carboxymethylhydroxyethyl guar, a carboxymethylhydroxypropylguar, an alkylcarboxyalkyl cellulose, an alkyl cellulose, an alkylhydroxyalkyl cellulose, a carboxyalkyl cellulose ether, a hydroxyethylcellulose, a carboxymethylhydroxyethyl cellulose, a carboxymethyl starch, a copolymer of 2-acrylamido-2-methyl-propane sulfonic acid and acrylamide, a terpolymer of 2-acrylamido-2-methyl-propane sulfonic acid, acrylic acid, acrylamide, or derivative thereof.

12. The fluid for treating a subterranean formation of claim 1, further comprising one or more components selected from the group consisting of a gel breaker, a buffer, a proppant, a clay stabilizer, a gel stabilizer, a surfactant and a bactericide.

13. A method of treating a subterranean zone penetrated by a well bore comprising:
providing a subterranean treating fluid comprising:
a solvent,
a crosslinkable component, and
a crosslinking composition comprising a spread crosslinker, the spread crosslinker having a first and a second headgroup separated by an intervening spacer that is covalently bound to the first and second headgroups, wherein
the first headgroup comprises at least one ring of at least five atoms, where at least two of the atoms in the at least one ring of the first headgroup are chelated polyvalent metal atoms, and
the second headgroup comprises at least one ring of at least five atoms, where at least two of the atoms in the at least one ring of the second headgroup are chelated polyvalent metal atoms; and
contacting the subterranean zone with the subterranean treating fluid.

14. The method of claim 13, wherein the spread crosslinker comprises one or more compounds obtained by reacting one or more chelating agents with a compound of formula I:

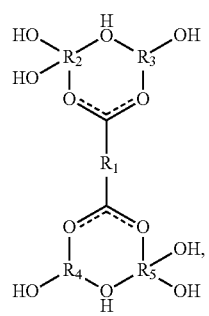

(I)

where
R$_1$ is:
an alkylene group having 1 to about 40 carbon atoms,
an arylene group having about 5 to about 40 carbon atoms,
an arylalkylene group having about 6 to about 40 carbon atoms, or
an alkylarylene group having about 6 to about 40 carbon atoms; and
R$_2$, R$_3$, R$_4$, and R$_5$ may be the same or different, and are selected from the group consisting of aluminum, zirconium, and titanium.

15. The method of claim 14, wherein the one or more chelating agent is selected from the group consisting of carboxylic acids, aminocarboxylic acids, polyols, alkanolamines, glutamic acid, lactic acid, triethanolamine, alanine, aspartic acid, oxalic acid, acetylacetonate, fumaric acid, bis-hydroxyethylglycine, maleic acid, tartaric acid, citric acid, nitrilotriacetic acid, hydroxyethyliminodiacetic acid, hydroxyethylethylenediaminetetraacetic acid, ethylenediaminetetraacetic acid, cyclohexylenediaminetetraacetic acid, diethylenetriaminepentaacetic, hydroxyethylethylenediaminetriacetic acid, diethylenetriaminepentaacetic acid, propylenediaminetetraacetic acid, ethylenediamindi(o-hydroxyphenylacetic) acid, ammonium salts thereof, lithium salts thereof, sodium salts thereof, and mixtures thereof.

16. The method of claim 13, wherein the spread crosslinker comprises one or more compounds obtained by reacting one or more chelating agents with a compound of formula II:

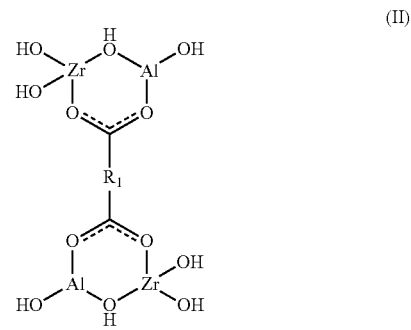

(II)

where R$_1$ is:
an alkylene group having 1 to about 40 carbon atoms, wherein hetero atoms either may or may not be present in the alkylene group;
an arylene group having about 5 to about 40 carbon atoms, wherein hetero atoms either may or may not be present in the arylene group;
an arylalkylene group having about 6 to about 40 carbon atoms, wherein hetero atoms either may or may not be present in either or both of the alkyl portion and the aryl portion of the arylalkylene group; or
an alkylarylene group having about 6 to about 40 carbon atoms, wherein hetero atoms either may or may not be present in either or both of the alkyl portion and the aryl portion of the alkylarylene group.

17. The method of claim 13, wherein the spread crosslinker comprises a compound of formula III:

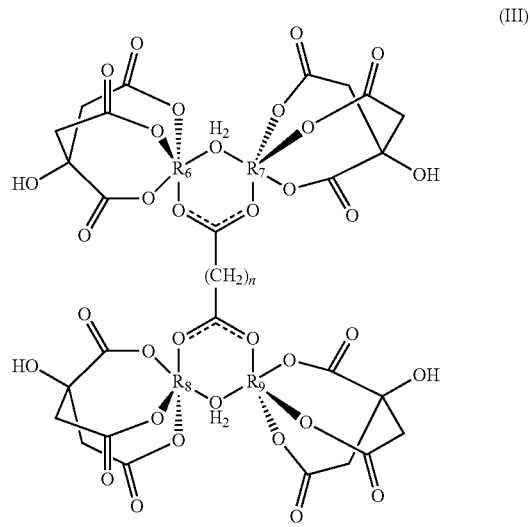

(III)

where n is an integer from 1 to about 40; and R$_6$, R$_7$, R$_8$ and R$_9$ may be the same or different, and are selected from the group consisting of aluminum, zirconium, and titanium.

18. The method of claim 13, wherein the crosslinkable component comprises a guar gum, a locust bean gum, a tara gum, a honey locust gum, a tamarind gum, a karaya gum, an arabic gum, a ghatti gum, a tragacanth gum, a carrageenen, a succinoglycan, a xanthan, a diutan, a hydroxylethylguar hydroxypropyl guar, a carboxymethylhydroxyethyl guar, a carboxymethylhydroxypropylguar, an alkylcarboxyalkyl cellulose, an alkyl cellulose, an alkylhydroxyalkyl cellulose, a carboxyalkyl cellulose ether, a hydroxyethylcellulose, a carboxymethylhydroxyethyl cellulose, a carboxymethyl starch, a copolymer of 2-acrylamido-2-methyl-propane sulfonic acid and acrylamide, a terpolymer of 2-acrylamido-2-methyl-propane sulfonic acid, acrylic acid, acrylamide, or derivative thereof.

19. The method of claim 13, wherein the subterranean treating fluid further comprises one or more components selected from the group consisting of a gel breaker, a buffer, a proppant, a clay stabilizer, a gel stabilizer, a surfactant and a bactericide.

20. The method of claim 13, wherein
the first headgroup contains two or more rings with each ring containing five, six, or seven atoms; and/or
the second headgroup contains two or more rings with each ring containing five, six, or seven atoms.

21. The method of claim 13, wherein
the chelated polyvalent metal atoms of the first headgroup are coordinated to a bidentate organic group or tridentate organic group, and/or
the chelated polyvalent metal atoms of the second headgroup are coordinated a bidentate organic group or tridentate organic group.

22. A method of controlling water in a subterranean formation, comprising:
introducing a crosslinkable fluid into a wellbore that penetrates a water-bearing subterranean formation, the crosslinkable fluid comprising:
a solvent,
a crosslinkable component, and
a spread crosslinker, wherein at least some of the crosslinkable fluid permeates a portion of the water-bearing subterranean formation, and the spread crosslinker comprises a compound of formula III:

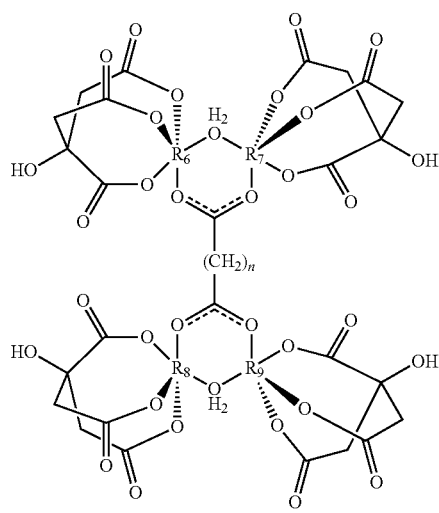

(III)

where n is an integer from 1 to about 40; and $R_6$, $R_7$, $R_8$ and $R_9$ may be the same or different, and are selected from the group consisting of aluminum, zirconium, and titanium.

23. The method of claim 22, wherein the crosslinkable component comprises a guar gum, a locust bean gum, a tara gum, a honey locust gum, a tamarind gum, a karaya gum, an arabic gum, a ghatti gum, a tragacanth gum, a carrageenan, a succinoglycan, a xanthan, a diutan, a hydroxylethylguar hydroxypropyl guar, a carboxymethylhydroxyethyl guar, a carboxymethylhydroxypropylguar, an alkylcarboxyalkyl cellulose, an alkyl cellulose, an alkylhydroxyalkyl cellulose, a carboxyalkyl cellulose ether, a hydroxyethylcellulose, a carboxymethylhydroxyethyl cellulose, a carboxymethyl starch, a copolymer of 2-acrylamido-2-methyl-propane sulfonic acid and acrylamide, a terpolymer of 2-acrylamido-2-methyl-propane sulfonic acid, acrylic acid, acrylamide, or derivative thereof.

24. A crosslinker composition, comprising:
a compound of formula IV:

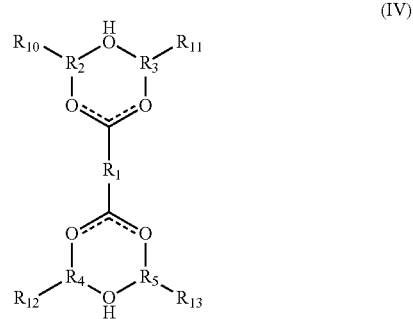

(IV)

where $R_1$ is:
an alkylene group having 1 to about 40 carbon atoms, wherein hetero atoms either may or may not be present in the alkylene group,
an arylene group having about 5 to about 40 carbon atoms, wherein hetero atoms either may or may not be present in the arylene group,
an arylalkylene group having about 6 to about 40 carbon atoms, wherein hetero atoms either may or may not be present in either or both of the alkyl portion and the aryl portion of the arylalkylene group, or
an alkylarylene group having about 6 to about 40 carbon atoms, wherein hetero atoms either may or may not be present in either or both of the alkyl portion and the aryl portion of the alkylarylene group;
$R_2$, $R_3$, $R_4$ and $R_5$ may be the same or different, and are selected from the group consisting of aluminum, zirconium, and titanium; and
$R_{10}$, $R_{11}$, $R_{12}$ and $R_{13}$ represent, independent from one another, a unidentate, bidentate, tridentate, or polydentate ligand system.

25. The crosslinker composition of claim 24, further comprising a crosslinkable component comprising a guar gum, a locust bean gum, a tara gum, a honey locust gum, a tamarind gum, a karaya gum, an arabic gum, a ghatti gum, a tragacanth gum, a carrageenan, a succinoglycan, a xanthan, a diutan, a hydroxylethylguar hydroxypropyl guar, a carboxymethylhydroxyethyl guar, a carboxymethylhydroxypropylguar, an alkylcarboxyalkyl cellulose, an alkyl cellulose, an alkylhydroxyalkyl cellulose, a carboxyalkyl cellulose ether, a hydroxyethylcellulose, a carboxymethylhydroxyethyl cellulose, a carboxymethyl starch, a copolymer of 2-acrylamido-2-methyl-propane sulfonic acid and acrylamide, a terpolymer of 2-acrylamido-2-methyl-propane sulfonic acid, acrylic acid, acrylamide, or derivative thereof.

26. The crosslinker composition of claim 24, further comprising one or more components selected from the group consisting of a gel breaker, a buffer, a proppant, a clay stabilizer, a gel stabilizer, a surfactant and a bactericide.

* * * * *